US00PP08261P

United States Patent [19]

van Andel

[11] Patent Number: Plant 8,261

[45] Date of Patent: Jun. 15, 1993

[54] ALSTROEMERIA NAMED STABUWIT

[75] Inventor: Jacob van Andel, Aalsmeer, Netherlands

[73] Assignee: Van Staavern B.V., Aalsmeer, Netherlands

[21] Appl. No.: 710,358

[22] Filed: Jun. 3, 1991

[51] Int. Cl.[5] ..... A01H 5/00

[52] U.S. Cl. ..... Plt./87.1

[58] Field of Search ..... Plt./68, 87.1

*Primary Examiner*—James R. Feyrer

*Attorney, Agent, or Firm*—Tilton, Fallon, Lungmus & Chestnut

[57] ABSTRACT

A new and distinct Alstroemeria cultivar particularly distinguished by its medium sized flowers, being irregularly and faintly, but distinctly covered with a faint pink blush, and which show distinct green shading at petal points which fade progressively toward the central portions of petals and are more intensive following the veining the parallel pair of the inside petals which are marked from base to tip with short, longitudinally extending dark brown pencil stripes which substantially fill the body area to provide a white flower having a distinctive dark center; the basal small outer petal of each flower also bears two minute, dark brown or purple pencil markings, one on each side of the tip portion, symmetrically, just inside the periphery of the margin; the central portions of the two inner petals include a broad, faint band of yellow or greenish-yellow; these flowers being carried on short, strong stems branching in a raceme manner from the upper portion of a tall main stem of a strong, upright bush.

1 Drawing Sheet

BACKGROUND OF THE NEW PLANT

This variety of Alstroemeria originated as a seedling of a hybrid produced in my nursery at Aalsmeer, Holland by my crossing of two plants selected from a field of various Alstroemeria varieties maintained at my nursery for breeding purposes. This particular seedling was selected from those produced by the said hybrid because of the pure white flower coloration on a plant having abundant foliage and very favorable growth characteristics. This selected seedling was propagated by me at Aalsmeer by dividing root stocks with very satisfactory results and thereafter this selected plant was propagated through several successive generations in the same manner which demonstrated conclusively that the novel characteristics of the originally selected seedling would be maintained from generation to generation and its homogeniety firmly established.

DESCRIPTION OF THE DRAWING

My new Alstroemeria variety is illustrated by the accompanying photographic drawing which, in full color, shows the form and coloration of the flowers as they appear with relatively close spacing in a raceme manner at the upper end of the flowering stem of the plant. The flower coloration shown being as nearly true to that herein specified as is reasonably possible to obtain by conventional photographic procedures.

DESCRIPTION OF THE NEW PLANT

The following is a detailed description of my new Alstroemeria variety as observed from plants grown under greenhouse conditions at Aalsmeer, Holland, with the stated flower color being according to the R.H.S. Colour Chart of The Royal Horticultural Society of London, England.

THE PLANT

Origin: Seedling.

Parentage:

*Seed parent.*—Breeding plant No. 4137-2. Breeding plant No. 4137-2 is colored pink, (RHS 63B), 120 cm.-140 cm.

*Pollen parent.*—Breeding plant No. 5309-1. Pollen parent plant No. 4137-2 is colored white, (RHS 155D), 180 cm.-200 cm.

Both of these parent plants are identified in permanent records maintained in the office at our Aalsmeer nursery and the production of the before-mentioned hybrid and the selected seedling are also recorded.

Classification:

*Botanaic.*—Alstroemeria hybrid.

*Commercial.*—Alstroemeria.

Form: A tall, upright bush.

Height: About 150 to 175 cm. depending upon season.

Main stem length: From about 150 to 175 cm.

Branching character: Normal.

Growth: Strong, vigorous and upright.

Foliage:

*Quantity.*—Abundant.

*Size of leaf.*—Length in summer, 14–18 cm., length in winter, 16–22 cm; width in summer, 2–3 cm., width in winter, 2–4 cm. '*Leaf shape.*—Broad elliptic with entire margins.

*Texture.*—Leathery.

*Color.*—Upper side — Middle Green (RHS 143A). Under side — Middle Green (RHS 144).

Rhizomes:

*Size.*—Varying according to the age of the plant.

*Color.*—White.

THE BUD

Size: Normal.

Diameter: About 1.5 cm.

Length: About 3.5 to 4 cm.

Form: Pear-shaped.

Peduncle:

*Length.*—About 5 cm.

THE FLOWER

Blooming habit: Continuous from Spring through Fall.
Flower size: Medium.
*Diameter.*—About 6.5 cm.
*Depth.*—About 5 cm.
Borne: Singly on a short stem branching in an upright manner as part of a raceme on the main stem.
Shape:
*When bloom first opens.*—A narrow funnel.
*When bloom matures.*—like a funnel with the petal tips curling outwardly.
Petalage:
*Number of petals.*—6.
Arrangement: Two concentric circles each having three petals, the outer petals being triangularly spaced and the inner petals being divided with a pair of them in substantially parallel relation and extending upwardly and the remaining single petal extending downwardly.
Form:
*Outer petals.*—Ovate with emarginate tips and lightly serrated margins.
*Inner petals.*—Long, ovate with mucronate tips and entire margins.
Texture: Soft.
Appearance: Satiny.
Color:
*Outer median petal front.*—Clean White 155D, with a spot of 62B tipped with 138D.
*Outer median petal reverse side.*—Clean White 155D with a spot of 63A/B tipped with 137B.
*Outer lateral petal front.*—Clean White 155D, spotted with 62B tipped with 138D.
*Outer lateral petals reverse side.*—Clean white — 155D, spotted with 63B tipped with 137D.
*Inner petals.*—Elliptical in shape with aristate tip and body color of White 155D.
*Inner lateral petals front.*—The parallel pair being marked overall with short Purple pencil stripes 59A, extending outwardly from the base toward the tip with a yellowish patch 8B in the middle of the petal and tipped with Pink 63D, with a greenish petal point 141C; the reverse side is Clean White 155D with a yellowish middle 1C, pinkish color at the tip 63B and greenish tip 141C.
*Inner median petal front.*—Clean White 155D has greenish base portion color 141C with 63D tip color and 2 dark purple marks, basal to tip 59D with a spot of yellow extending from the tip to mid-petal of greenish color 63B with tip point 141C.
Flower stem:
*Length.*—About 5 to 6 cm.
*Color.*—Light Green.
Persistence: The flowers hang on and dry.
Fragrance: None.
Lasting quality:
*On the plant.*—About 21 days.
*As a cut flower.*—About 15 days.

THE REPRODUCTIVE ORGANS

Stamens:
*Number.*—Six.
*Arrangement.*—One opposite each petal.
*Anthers.*—Size: About 8 mm. Color: Grey.
*Filaments.*—Length: About 3.5 cm. Color: Pink.
*Pollen.*—Color: Grey/Black.
Pistils:
*Number.*—One.
Style:
*Length.*—Varies with age.
*Color.*—Pink.
*Stigma.*—Color: Pink.
Character of ovaries: Ovaries have anthocyanics.

FRUIT

Fertility: The fruit is fertile.
Shape: Capsular.
Color: Light brown.

I claim:

1. A new and distinctive hybrid Alstroemeria variety, substantially as herein shown and described, characterized in particular by its Clean White flowers, the outer median and lateral petals of which have outwardly curled mucronate tips with a faint pink blush, which show distinct green shading at petal points which fade progressively toward the central portions of the petals and are more intensive following the veining; the inner median petal is characterized by Clean White petal with a greenish shading at the base and light pinkish coloration at the tip and two minute, dark purple pencil markings on either side of the tip portion, symmetrically just inside the periphery of the margin, ending with green tip points and, the inner lateral petals are Clean White with many short, longitudinally extending purple pencil stripes, extending almost to the mucronate petal end, having a greenish base, with a yellowish portion in the middle, and a pinkish tip.

* * * * *

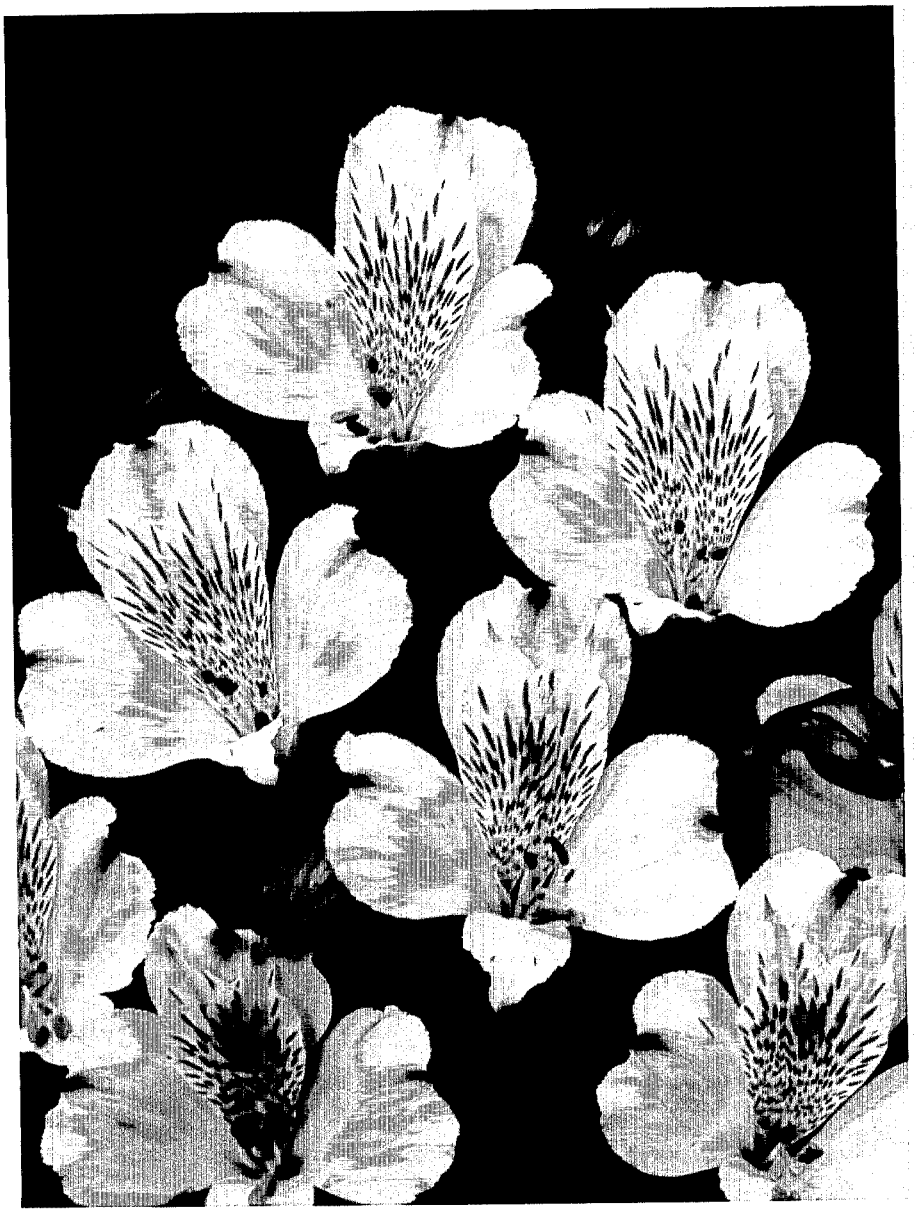

UNITED STATES PATENT AND TRADEMARK OFFICE

CERTIFICATE OF CORRECTION

PATENT NO. : PP 08,261

DATED : June 15, 1993

INVENTOR(S) : van Andel

It is certified that error appears in the above-indentified patent and that said Letters Patent is hereby corrected as shown below:

On the title page, item [57] Abstract, line 7, after "following the veining" insert --of--.

Column 2, line 25, delete " ' ".

Signed and Sealed this

Twenty-second Day of February, 1994

*Attest:*

Bruce Lehman

BRUCE LEHMAN

*Attesting Officer*

*Commissioner of Patents and Trademarks*